United States Patent [19]

Torrie et al.

[11] Patent Number: 5,667,513

[45] Date of Patent: Sep. 16, 1997

[54] SOFT TISSUE ANCHOR DELIVERY APPARATUS

[75] Inventors: Paul A. Torrie, Marblehead, Mass.; Graham Smith, Plaistow, N.H.

[73] Assignee: Smith & Nephew Dyonics Inc., Andover, Mass.

[21] Appl. No.: 472,509

[22] Filed: Jun. 7, 1995

[51] Int. Cl.$^6$ ................................................. A61B 17/00

[52] U.S. Cl. ................... 606/104; 606/151; 606/213; 606/232; 81/3.4; 81/44; 81/453

[58] Field of Search ............................. 606/104, 75, 73, 606/72, 60, 232, 205, 207, 213, 151; 604/106, 107; 81/2.4, 44, 53.2, 453, 452, 451

[56] References Cited

U.S. PATENT DOCUMENTS

| | | | |
|---|---|---|---|
| 2,579,438 | 12/1951 | Longfellow | 81/453 |
| 4,165,772 | 8/1979 | Suga | 81/453 |
| 4,884,572 | 12/1989 | Bays et al. | |
| 4,895,148 | 1/1990 | Bays et al. | 606/213 |
| 4,924,865 | 5/1990 | Bays et al. | 606/77 |
| 4,968,315 | 11/1990 | Gatturana | 606/232 |
| 5,107,573 | 4/1992 | Zhang | 24/109 |
| 5,139,499 | 8/1992 | Small et al. | 606/73 |
| 5,380,334 | 1/1995 | Torrie et al. | 606/75 |

FOREIGN PATENT DOCUMENTS

| | | | |
|---|---|---|---|
| 238724 | 9/1986 | Germany | 606/104 |
| 1053820 | 11/1983 | U.S.S.R. | 606/104 |

*Primary Examiner*—Jeffrey A. Schmidt
*Attorney, Agent, or Firm*—Pravel, Hewitt, Kimball & Krieger

[57] ABSTRACT

A soft tissue anchor delivery apparatus includes a gripping device having fingers at the distal end and configured such that they can hold a soft tissue anchor about the head portion of the anchor. An actuating tube slides over the gripper and the fingers, thus holding the fingers and the contained soft tissue anchor within the bore of the actuating tube. A pushrod is placed within the bore of the gripper. The pushrod has a countersunk head that is shaped such that it is a close fit for the head of the soft tissue anchor. The pushrod is connected to a tube having a bore so that the actuating pin of the soft tissue anchor can be pushed down into the head of the anchor. The pushrod is spring loaded so as to allow the pushrod to be driven distally upon retraction of the actuating tube, thus driving the anchor free of the deployed fingers and hence of the entire delivery system.

29 Claims, 6 Drawing Sheets

SOFT TISSUE ANCHOR DELIVERY APPARATUS

BACKGROUND OF THE INVENTION

1. Field of the Invention

The present invention relates to orthopedic surgical instruments and more particularly a soft tissue anchor delivery apparatus for inserting a soft tissue anchor into a patient's joint tissue (for example, glenoid) to effect a soft tissue repair. Even more particularly, the present invention relates to an improved soft tissue anchor delivery system that comprises an instrument body that includes a plurality of gripper fingers mounted on the distal end of a tube and configured such that when held in a closed position they form a support under the enlarged head of a soft tissue anchor, the gripping fingers being contained about the soft tissue anchor using an actuating tube that slides over the combination of the fingers, soft tissue anchor, and a pushrod and wherein the pusher is spring loaded as to allow the pusher to be driven distally upon retraction of the actuating tube, driving the anchor free of the deployed fingers into a surgically formed opening.

2. General Background

Small soft tissue anchors and small tissue repair tacks are used to repair certain bodily tissues. As part of a surgical repair procedure, a surgeon uses a K-wire to drill through a first section of soft tissue that is to be attached to a second section of tissue (for example, the glenoid). The K-wire drills through both the tissue to be attached and the glenoid using a K-wire. The surgeon over drills the K-wire through the soft tissue and into the middle of the glenoid forming a surgical opening for receiving the soft tissue anchor. This procedure allows the surgeon to place an anchor into the surgically formed opening. Tissue anchors and repair tacks usually include an elongated hollow shank, and an enlarged head, and an expansion or actuating pin that enters a longitudinal bore of the shank and head. When the actuating pin enters the bore, it spreads the shank creating a tight fit with the surrounding tissue at the surgically formed opening.

A number of patents have issued for soft tissue anchors and repair tacks used for treating and repairing torn bodily material in vivo. For example, U.S. Pat. No. 4,924,865 "REPAIR TACK FOR BODILY TISSUE" discloses an apparatus for repairing in-vivo torn cartilaginous or other bodily tissue during a surgical procedure. The '865 patent employs a repair tack of bio-degradable material chosen to have a degradation time in excess of the required healing time for the tissue. The repair tack has a shaft or shank portion with a longitudinal bore and a grip or enlarged head portion adapted for releasable engagement by an applicator instrument. In one embodiment, the grip portion of the tack is a cross bar at the proximal end of the shank or shaft which fits into an open sided slot at the forward end of the applicator. U.S. Pat. No. 4,924,865 is incorporated herein by reference.

Another patent that relates to repair tacks and a method of joining torn parts of bodily tissue in vivo is U.S. Pat. No. 4,895,148. The '148 patent discloses a method for repairing in vivo torn cartilaginous or other bodily tissue, particularly torn meniscus tissue, during arthroscopic surgery. The '148 patent employs a repair tack of biodegradable material chosen to have a degradation time in excess of the required healing time for the tissue. The repair tack has a shaft portion with a longitudinal bore and a grip portion adapted for releasable engagement by a hollow applicator. In one embodiment the grip portion of the tack is a cross bar, at the proximal end of the shaft, which fits into an open-sided slot at the forward end of the applicator. A needle passes through the hollow applicator and tack bore to project from the distal end of the tack shaft. With the tack supported in the slot and the needle passing through the stem, the needle and tack can be inserted into the joint cavity through a portal in the skin or through an insertion cannula. The sharpened needle point is placed in contact with the torn tissue and force is applied to the holder and the needle to cause the needle and the tack to penetrate the tissue to a desired depth. The point of the needle is withdrawn into the axial opening of the applicator and the cross bar is displaced from the slot, thereby leaving the tack firmly secured in the tissue. U.S. Pat. No. 4,495,148 is incorporated herein by reference.

An applicator for treating torn bodily material in-vivo is disclosed in U.S. Pat. No. 4,884,572 entitled "TACK AND APPLICATOR FOR TREATING TORN BODILY MATERIAL IN VIVO". The '572 patent discloses an apparatus for repairing in-vivo torn torn cartilaginous or other bodily tissue, particularly torn meniscus tissue during arthroscopic surgery, employs a repair tack of biodegradable material chosen to have a degradation time in excess of the required healing time for the tissue. The repair tack has a shaft portion with a longitudinal bore and a grip portion adapted for releasable engagement by a hollow applicator. In one embodiment the grip portion of the tack is a cross bar, at the proximal end of the shaft, which fits into an open-sided slot at the forward end of the applicator. A needle passes through the hollow applicator and tack bore to project from the distal end of the tack shaft. U.S. Pat. No. 4,884,572 is incorporated herein by reference.

Most prior art instruments for placing and inserting repair tacks and soft tissue anchors are awkward to use and inefficient. The present invention provides an improvement to prior art methods and apparatus for delivery of soft tissue anchors.

SUMMARY OF THE INVENTION

The present invention relates to an improved soft tissue anchor delivery system. The present invention uses a plurality of gripper fingers that extend from the distal end of an elongated tube. The tube preferably has four fingers at the distal end configured such that when held in closed position they form a support under the head of the soft tissue anchor.

An actuating tube slides over the combination of the fingers and the inner "gripper" tube to which the fingers are attached. The actuating tube holds the fingers in closed position during insertion of the anchor. Upon retraction of the actuating tube, the fingers are exposed and allowed to spring open, thus freeing a spring loaded pushrod to eject the anchor.

The pusher is an elongated, spring loaded pushrod structure. At the distal end of pushrod there is provided a countersunk head shaped such that it is a close fit for the head of the anchor.

The countersunk end of the pusher is connected to a tube having a bore such that the actuating pin of the anchor can be pushed through it into the head of the anchor.

The pushrod is spring loaded with a coil spring that allows the pushrod to be driven distally upon retraction of the actuating tube, thus driving the anchor free of the deployed fingers and hence of the delivery system.

During surgical operation, the surgeon first drills a hole of predetermined size using an over drill that tracks over a guide wire or K-wire. The over drill is then removed leaving the guide wire or K-wire in situ. The delivery apparatus of the present invention is then assembled with a soft tissue anchor in place. The assembled delivery system with anchor in place is slipped over the K-wire or guide wire and pushed or tapped through the soft tissue into this surgically formed hole.

The guide wire is removed and the actuating pin loaded down the bore of the pushrod. The actuating pin is then driven into place using a metallic drive wire (for example 0.062 inch diameter).

The actuating tube is then retracted proximally allowing the fingers to spread and the spring loaded pushrod to eject the anchor.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
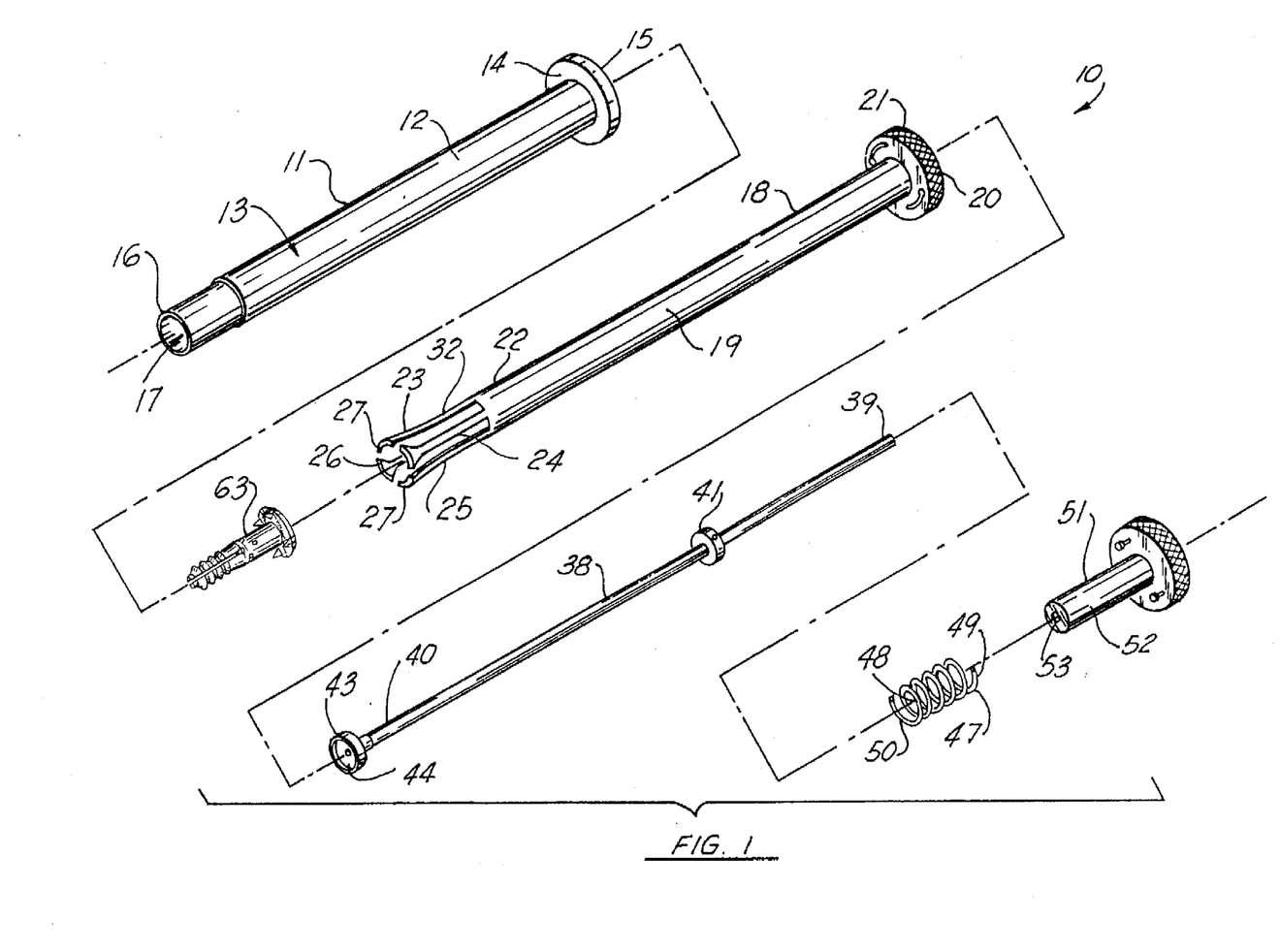
FIG. 1 is a perspective exploded view of the preferred embodiment of the preferred embodiment of the apparatus of the present invention.

FIG. 1 illustrates generally the preferred embodiment of the apparatus of the present invention designated generally by the numeral 10. Soft tissue anchor delivery apparatus 10 includes an outer actuation tube or sleeve 11 that is generally cylindrically shaped. Actuation tube 11 provides a cylindrical wall 12 having a cylindrical outer surface 13. An annular flange 14 is provided at the proximal end 15 of tube 11. During use, the surgeon grips and moves flange 14 when triggering the delivery apparatus 10 to release a soft tissue anchor.

The tube 11 has a proximal end 15 and a distal end 16. Tube 11 provides a cylindrically shaped open ended bore 17. The tube 11 is an actuation tube that slides upon an inner gripper tube 18 when triggering the apparatus 10 to dispense a soft tissue anchor.

A gripper 18 defines an inner tube or sleeve that fits snugly but can slide within the bore 17 of outer tube 11. Gripper 18 has a proximal end 21 and a distal end 22. Gripper 18 has a generally cylindrically shaped wall portion 19 with an annular flange 20 at the proximal end portion thereof. Distal end 22 carries a plurality of gripping fingers 23–26. Each of fingers 23–26 has an end portion 27 that is shaped to register against the under side of a soft tissue anchor 63.

Each finger end portion 27 has an arcuate edge 28, a pair of radial edges 29, an arcuate shoulder 30, and a triangular plate portion 31. An elongated longitudinal strut 32 of each finger 23–26 defines an attachment with the cylindrical wall of the gripper 18.

Gripper 18 has a longitudinal open ended bore 33 that is generally cylindrically shaped. Circular flange 20 has arcuate slots 34, 35 each having a circular portion 36, 37 as shown in the drawings.

A pushrod 38 is slidably mounted during use within the bore 33 of gripper 18. Pushrod 38 has a proximal end 39 and a distal end 40. An annular flange 41 is disposed at the middle 42 section of pushrod 38. A second annular flange 43 is disposed at the distal end 40 of pushrod 38. Annular flange 43 provides a concave surface 44 that is sized and shaped to engage the upper surface of the head of the soft tissue anchor to be inserted in the patient's tissue. Second annular flange 43 also provides an annular shoulder 45 that is sized and shaped to encircle and mate with the head of the soft tissue anchor to be inserted.

Pushrod 38 has an elongated, cylindrically shaped open ended bore 46 that can receive an actuating pin and a driver that will insert the actuating pin into a bore of the soft tissue anchor. Coil spring 47 is placed about proximal end 39 of pushrod 38. Coil spring 47 has a spring bore 48 that encircles the proximal end 39 of pushrod 38. Coil spring 47 has end portions including a proximal end 49 and a distal end 50. The distal end 50 registers against the first annular flange 41. The proximal end 49 of coil spring 47 registers against boss 51.

Boss 51 has a tubular portion 52 that is generally cylindrically shaped. The cylindrically shaped tubular portion 52 is hollow, providing a cylindrically shaped open ended bore 53. The boss 51 tubular portion has a cylindrical wall 54. At one end portion of the cylindrical wall 54 there is provided an annular flange 55 having a pair of locking posts 56, 57 thereon. Each of the locking posts 56, 57 includes a smaller diameter portion and a larger diameter portion. In the drawings, the smaller diameter portion 58 and larger diameter portion 59 are provided for locking post 56. Smaller diameter portion 60 and larger diameter portion 61 are provided for the locking post 57.

Figures 2, 3, 4, 5, 6:
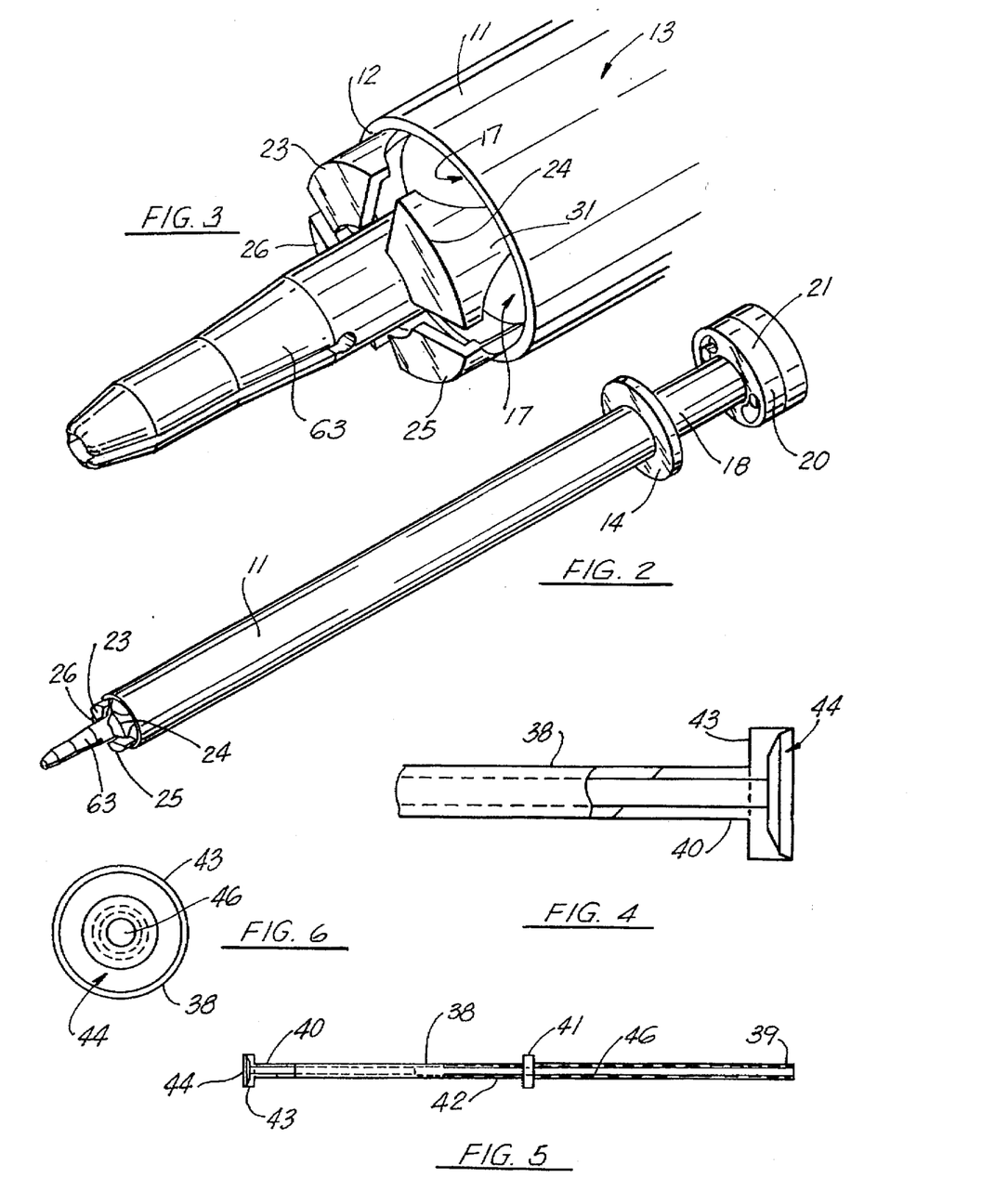
FIG. 2 is a perspective view of the preferred embodiment of the apparatus of the present invention.
FIG. 3 is a partial perspective view of the preferred embodiment of the apparatus of the present invention.
FIG. 4 is a fragmentary, partial sectional view of the preferred embodiment of the apparatus of the present invention illustrating the pushrod.
FIG. 5 is a side sectional view illustrating the portion of the preferred embodiment of the apparatus of the present invention.
FIG. 6 is an end view of the pushrod portion of the preferred embodiment of the apparatus of the present invention.
Figure 7:
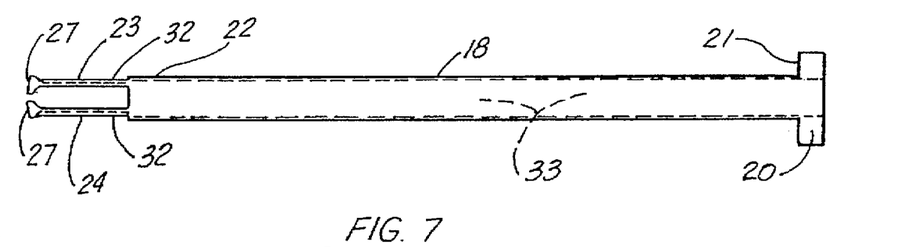
FIG. 7 is a side view of the gripper tube portion of the preferred embodiment of the apparatus of the present invention.
Figure 8:
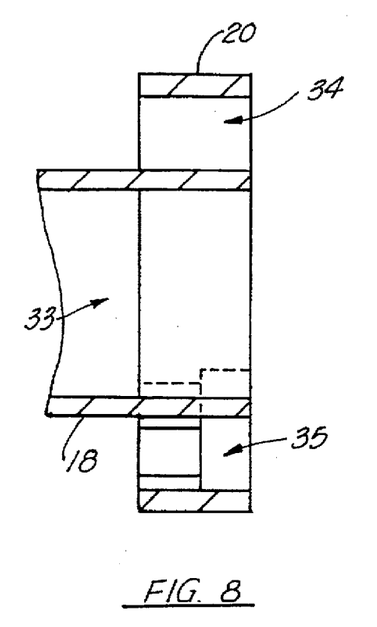
FIG. 8 is a side, fragmentary view of the gripper portion of the preferred embodiment of the apparatus of the present invention.
Figure 11:
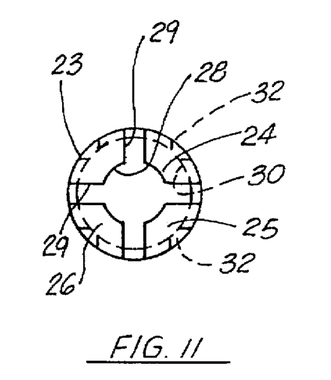
FIG. 11 is an end view of the gripper portion of the preferred embodiment of the apparatus of the present invention.
Figure 12:
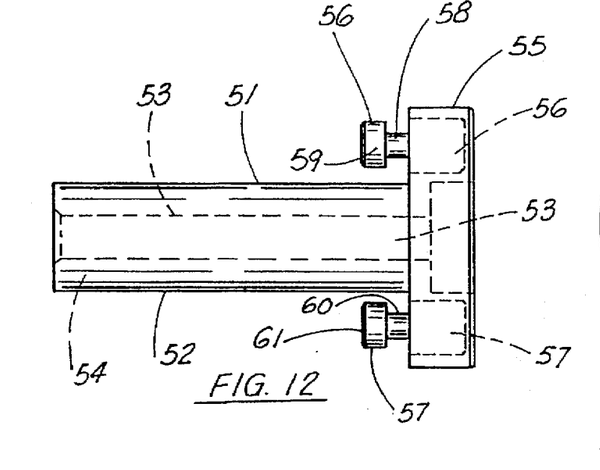
FIG. 12 is a side view of the locking boss portion of the preferred embodiment of the apparatus of the present invention.
Figure 13:
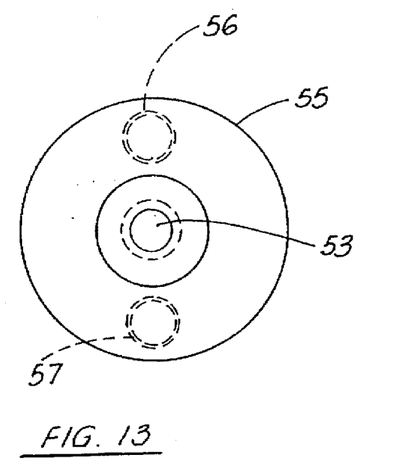
FIG. 13 is an end view of the locking boss portion of the preferred embodiment of the apparatus of the present invention.
Figure 14:
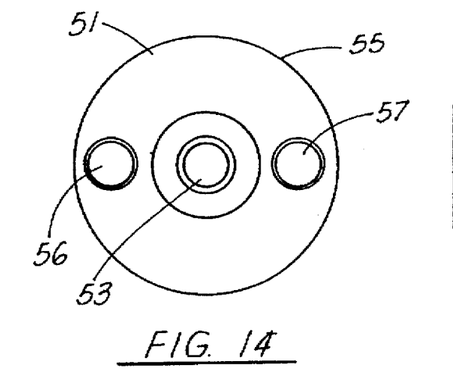
FIG. 14 is an end view of the locking boss portion of the preferred embodiment of the apparatus of the present invention.
Figure 15:
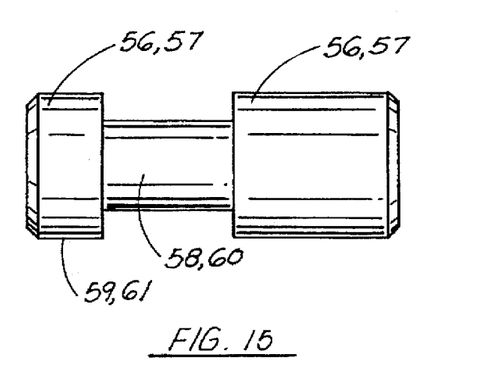
FIG. 15 is a fragmentary side view illustrating one of the locking pin portions of the locking boss.
Figure 17:
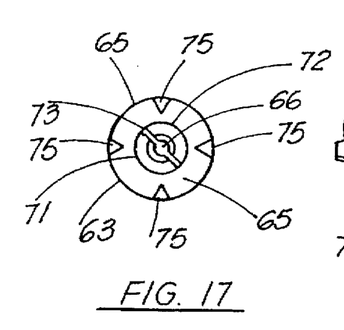
FIG. 17 is an end view of the soft tissue anchor portion of the preferred embodiment of the apparatus of the present invention.
Figure 18:
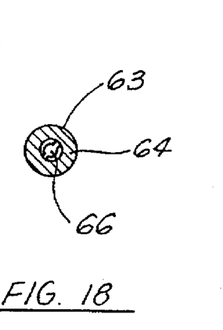
FIG. 18 is a sectional view taken along lines 18—18 of FIG. 16.

The locking posts 56, 57 engage the arcuate slots 34, 35 to spring load pushrod 38. Boss 51 is used to spring load pushrod 38. During use, the user first assembles the soft tissue anchor 63 to gripper 18 by surrounding the head 65 of soft tissue anchor 63 with the plurality of fingers 23–27. Each of the fingers 23–37 as shown in FIG. 11 nests in between two of the teeth 75 as shown in FIG. 17. This position is shown in FIGS. 2 and 3 of the drawings. The user then places the gripper and the held soft tissue anchor 63 within the bore 17 of actuating tube 11. The head 65 of soft tissue anchor 63 when gripped by fingers 23–27 forms a tight fit with inner bore 17 of tube 11. This tight fit is a frictional fit that is not overcome by the coil spring 47 once pushrod 38 is spring loaded with boss 51. Rather, the user must move flanges 14, 20 together using his or her fingers 82, 83 (see FIG. 24) to trigger the apparatus 10 and thus deliver a soft tissue anchor 63.

To spring load the apparatus 10, pushrod 38 is placed within bore 17 of actuating tube 11. Flange 43 of pushrod 38 is placed in contact with the head 65 of soft tissue anchor 63. The concave surface (see FIG. 4) of pushrod 38 closely conforms to the head 65 (see FIG. 16). In order to spring load the pushrod, the user then places coil spring 47 about the proximal 39 end of pushrod 38 as the pushrod 38 sits within bore 17 of actuating tube 11 and the flange 43 against soft tissue anchor 63.

Figure 9:
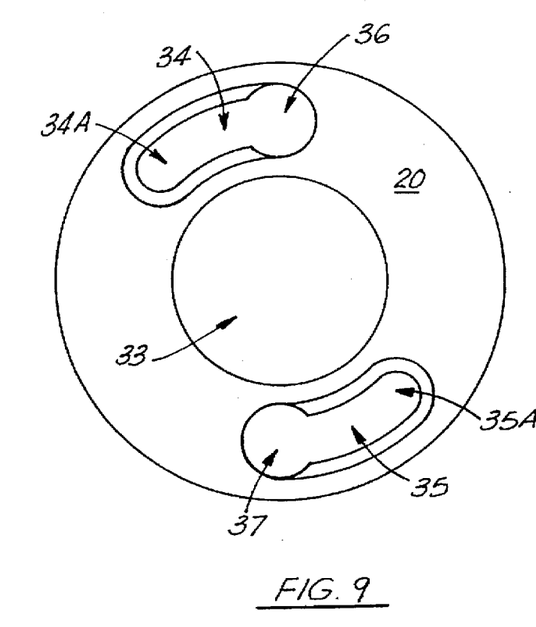
FIG. 9 is an end view of the gripper portion of the preferred embodiment of the apparatus of the present invention.
Figure 10:
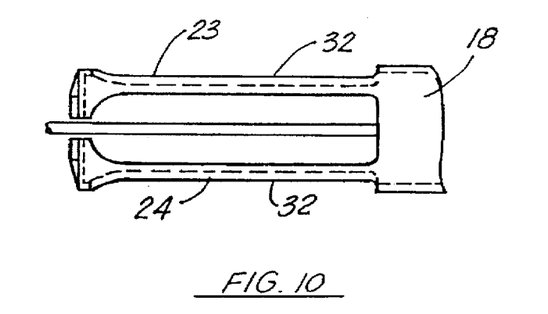
FIG. 10 is a fragmentary side view illustrating the distal end of the gripper portion of the preferred embodiment of the apparatus of the present invention.

The coil spring 47 is compressed when boss 51 presses against the proximal 49 end of coil spring 47 compressing it against flange 41 of pushrod 38. The locking posts 56, 57 are inserted into the circular portions 36, 37 of slots 34, 35. The boss 51 is then rotated until the smaller diameter sections 58, 60 of posts 56, 57 register with the narrowed thickness portions of slot 34, 35 designated as 34A, 35A respectively in the drawings (see FIG. 9). The larger diameter portions 59, 61 of posts 56, 57 are larger in diameter than the thickness of slots 34, 35 at positions 34A, 35A. The final locking position is shown in FIG. 2 of the drawings.

Figure 24:
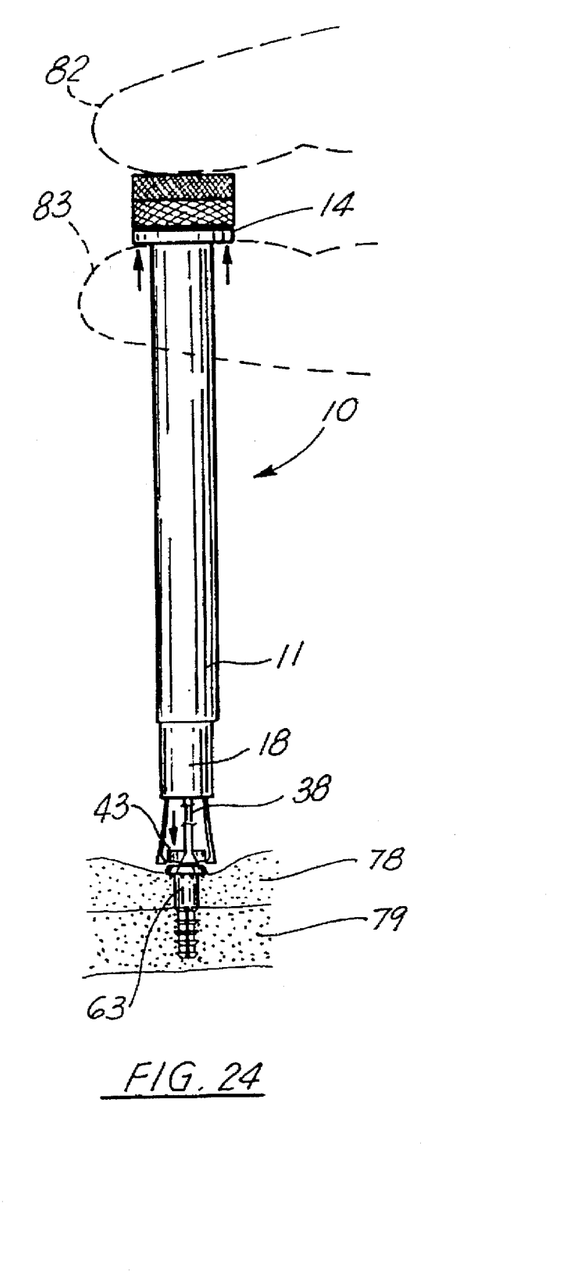

In order to release the soft tissue anchor 63, the surgeon simply pulls on the flanges 14, 20 together using his or her fingers 82, 83 overcoming friction between outer tube 11 and gripper 18 holding anchor 63. This causes the actuating tube 11 to slide upon the gripper 18 and thrusts the fingers 23–26 beyond the distal end 16 of actuating tube 11. The fingers 23–26 are then allowed to expand and the pushrod 38 presses against the soft tissue anchor 63 releasing it as shown in FIG. 24.

An elongated circular pushrod 62 is provided for loading an actuating pin down the bore of the pushrod 38. Pushrod 38 also drives the actuating pin into the bore of soft tissue anchor 63. Pushrod 62 can be for example a 0.062" diameter metallic cylindrical drive wire that fits the bore of pushrod 38.

Figure 16:
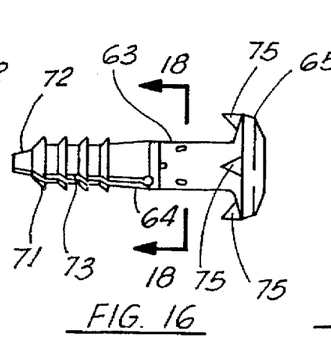
FIG. 16 is a side view of the soft tissue anchor portion of the preferred embodiment of the apparatus of the present invention.

Soft tissue anchor 63 includes an elongated shank 64 and an enlarged head 65. An open ended cylindrically shaped bore 66 extends from the top of soft tissue anchor 63 to the bottom thereof. The elongated open ended bore 66 extends through both the elongated shank 64 and the enlarged head 65. Open ended bore 66 receives an actuating pin 73 for locking the soft tissue anchor 63 into a surgically formed opening that is drilled by the surgeon. Elongated shank 64 can provide a plurality of annular teeth or rings 68–70 that enhance a gripping of the soft tissue anchor 63 into the surrounding tissue.

Elongated shank 64 is preferably provided in the form of a pair of halves 71, 72 separated by longitudinal slot 73. This construction allows the shank halves 71, 72 to move apart when actuating pin 74 is placed in the bore 66 of the soft tissue anchor 63. The enlarged head 65 can be provided with a plurality of circumferentially spaced wedge shaped teeth 75. Teeth 75 that enhance a gripping connection between the soft tissue anchor 63 and the surrounding tissue.

Figures 19, 20, 21, 22, 23:
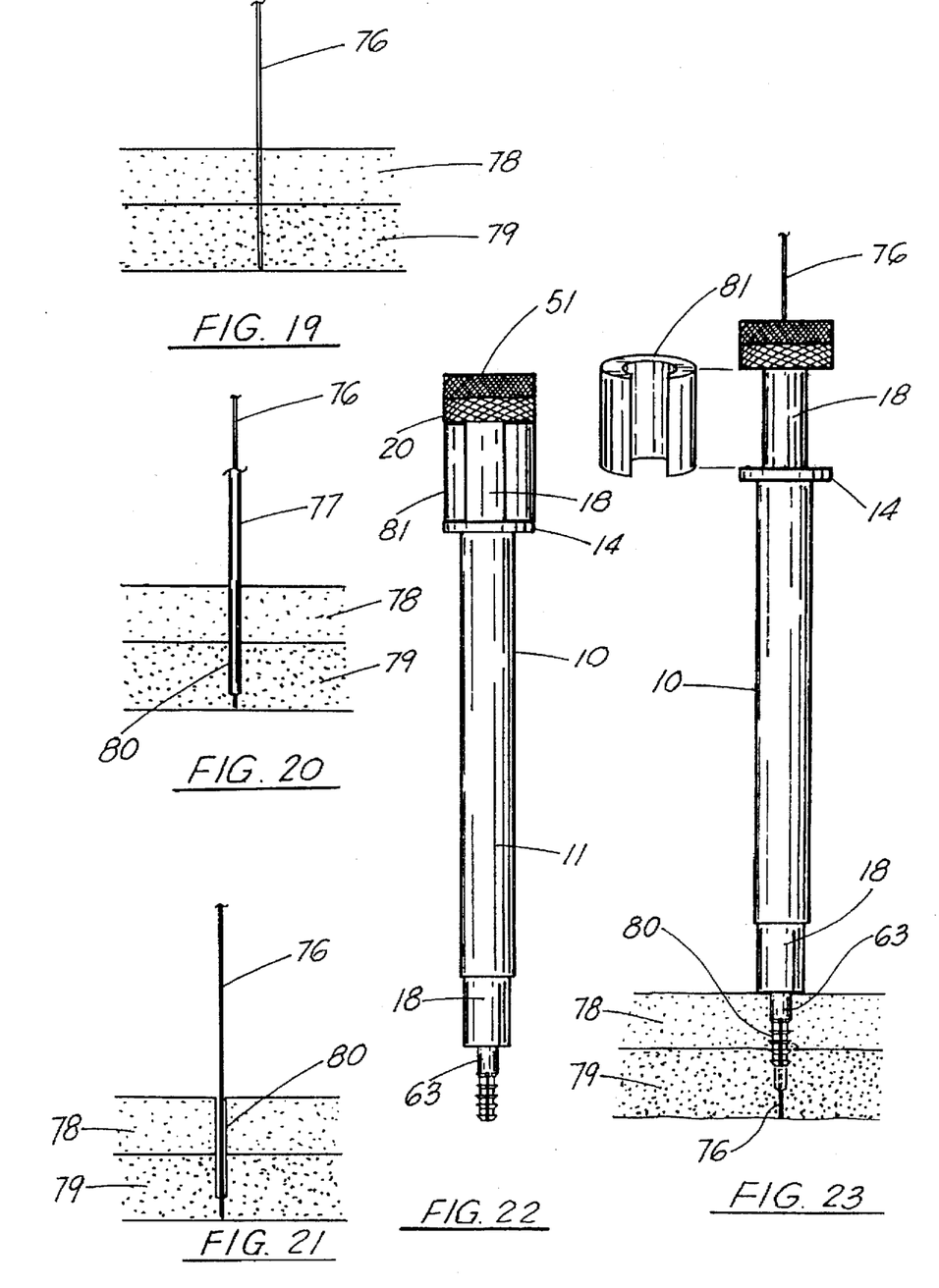
FIG. 19–26 are schematic elevational views that illustrate the surgical method of the present invention.

The surgical technique is illustrated in the drawings in FIGS. 19–26. A K-wire 76 is first used to form a surgical opening through the tissue that is to be attached. The surgeon also drills through and into the surrounding tissue (glenoid for example) with the K-wire 76. In FIG. 19, the tissue layers to be attached are designated as 78, 79. The surgeon then drills over the K-wire through the soft tissue layer 78 and into the middle of the glenoid 79 with an over-drill 77. The surgeon then removes the over-drill 77, leaving the K-wire 70 sticking out of the glenoid layer 79 and through the soft tissue layer 78 to be attached (see FIG. 21). The surgeon then uses the apparatus 10 of the present invention with the soft tissue anchor 63 attached. The surgeon slides the apparatus 10 over the K-wire through the soft tissue (see FIG. 23) and into the surgically formed opening 80 that was drilled with the over drill.

Figure 25:
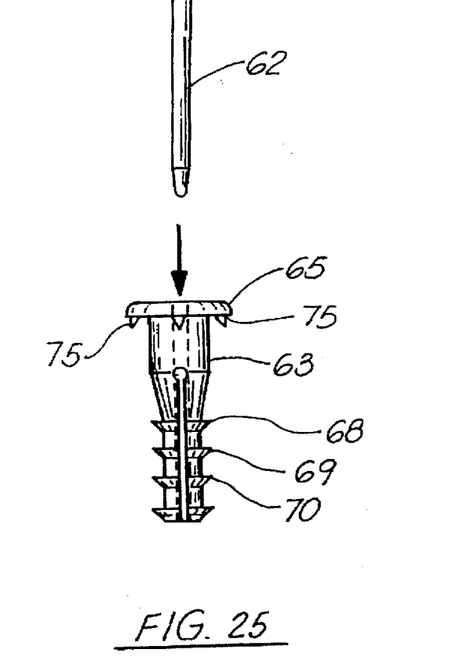
Figure 26:
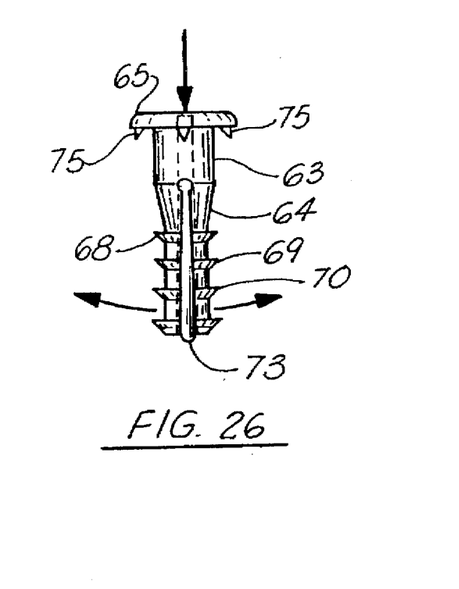

The K-wire 76 is removed and the actuating pin 74 is inserted into the bore 46 of pushrod 38. The actuating pin 74 is then pushed down the bore of the pushrod and into the bore 66 of the soft tissue anchor 63. Drive rod 62 is placed into the bore of the pushrod 38 so that the drive rod 62 can push the actuating pin 74 into the soft tissue anchor bore 66. Once this is accomplished, the surgeon releases the soft tissue anchor 10 by releasing the locking sleeve 81 and then pulling the outer sleeve 11 back and towards the flange of the gripper 18. This allows the pushrod 38 and soft tissue anchor 63 to advance and exposes the fingers 23–26. Once the fingers 23–26 are exposed beyond the distal end 16 actuating sleeve 11, fingers 23–26 can spring open to allow the spring loaded pushrod 38 to release the soft tissue anchor 63. The following table lists the parts numbers and parts descriptions as used herein and in the drawings attached hereto.

| PARTS LIST | |
|---|---|
| Part Number | Description |
| 10 | delivery system |
| 11 | outer tube |
| 12 | cylindrical wall |
| 13 | cylindrical outer surface |
| 14 | annular flange |
| 15 | proximal end |
| 16 | distal end |
| 17 | open ended bore |
| 18 | gripper |
| 19 | cylindrical wall |
| 20 | annular flange |
| 21 | proximal end |
| 22 | distal end |
| 23 | finger |
| 24 | finger |
| 25 | finger |

-continued

PARTS LIST

| Part Number | Description |
|---|---|
| 26 | finger |
| 27 | finger end portion |
| 28 | arcuate edge |
| 29 | radial edge |
| 30 | arcuate shoulder |
| 31 | triangular plate |
| 32 | longitudinal strut |
| 33 | longitudinal bore |
| 34 | arcuate slot |
| 35 | arcuate slot |
| 36 | circular portion |
| 37 | circular portion |
| 38 | pushrod |
| 39 | proximal end |
| 40 | distal end |
| 41 | annular flange |
| 42 | middle |
| 43 | annular flange |
| 44 | concave surface |
| 45 | annular shoulder |
| 46 | pushrod bore |
| 47 | coil spring |
| 48 | spring bore |
| 49 | proximal end |
| 50 | distal end |
| 51 | boss |
| 52 | tubular portion |
| 53 | open ended bore |
| 54 | cylindrical wall |
| 55 | annular flange |
| 56 | locking post |
| 57 | locking post |
| 58 | smaller diameter portion |
| 59 | larger diameter portion |
| 60 | smaller diameter portion |
| 61 | larger diameter portion |
| 62 | circular pushrod |
| 63 | soft tissue anchor |
| 64 | elongated shank |
| 65 | enlarged head |
| 66 | open ended bore |
| 67 | longitudinal slot |
| 68 | annular ring |
| 69 | annular ring |
| 70 | annular ring |
| 71 | shank half |
| 72 | shank half |
| 73 | longitudinal slot |
| 74 | actuating pin |
| 75 | wedge shaped teeth |
| 76 | k-wire |
| 77 | over-drill |
| 78 | tissue layer |
| 79 | tissue layer |
| 80 | drilled opening |
| 81 | locking sleeve |
| 82 | user's finger |
| 83 | user's finger |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A soft tissue anchor delivery apparatus for inserting a soft tissue anchor that includes an elongated shank and an enlarged head, comprising:

a) an outer tube having an elongated bore and proximal and distal end portions;

b) an inner tube that fits the bore of the outer tube, said inner tube having a proximal end, a distal end, a handle and a longitudinal inner tube bore;

c) said inner tube having a plurality of fingers at the distal end portion thereof, said fingers being shaped to grip the soft tissue anchor member at the enlarged head portion thereof;

d) said plurality of fingers being biased to expand radially when moving from a position inside the bore of the larger tube to a position outside the bore of the larger tube;

e) a pushrod slidably disposed within the bore of the inner tube, said pushrod having proximal and distal end portions, said distal end portion having means for engaging said head of said soft tissue anchor, the pushrod being operable to drive the soft tissue anchor free of the fingers when the fingers exit the distal end of the outer tube; and f) wherein the inner tube handle comprises a pair of interlocking members.

2. The soft tissue anchor delivery apparatus of claim 1 further comprising spring means for driving the pushrod distally upon retraction of the outer tube relative to the inner tube.

3. The soft tissue anchor delivery apparatus of claim 1 wherein the outer tube bore has a constant internal diameter.

4. The soft tissue anchor delivery apparatus of claim 1 wherein the fingers are circumferentially spaced about the wall of the inner tube.

5. The soft tissue anchor delivery apparatus of claim 1 wherein there are at least two of the fingers.

6. The soft tissue anchor delivery apparatus of claim 1 wherein the fingers extend longitudinally from the distal end of the inner tube.

7. The soft tissue anchor delivery apparatus of claim 1 further comprising a handle affixed to the proximal end of the inner tube for manipulating the inner tube relative to the outer tube.

8. The soft tissue anchor delivery apparatus of claim 1 wherein the inner tube handle interlocking members include a first member that is attached to the proximal end of the inner tube and a second member that fits the inner tube bore.

9. The soft tissue anchor delivery apparatus of claim 1 wherein the pushrod comprises an elongated member having a transversely extending flange positioned between the end portions of the elongated member.

10. The soft tissue anchor delivery apparatus of claim 9 further comprising a spring that moves the pushrod during use, wherein the pushrod flange receives one end of the spring.

11. The soft tissue anchor delivery apparatus of claim 10 wherein the spring means comprises a coil spring.

12. The soft tissue anchor delivery apparatus of claim 11 wherein the spring is mounted about the elongated member of the pushrod, one end of the spring engaging the flange.

13. The soft tissue anchor delivery apparatus of claim 9 wherein the elongated member has a pair of flanges mounted thereon, one flange positioned between the end portions of the elongated member an a second flange positioned at the distal end of the elongated member, wherein the second flange comprises said means for engaging the head of the soft tissue anchor during use.

14. The soft tissue anchor delivery apparatus of claim 1 further comprising a spring holder that supports the spring means during use, said spring means and spring holder each fitting the inner tube bore.

15. A soft tissue anchor delivery apparatus for inserting a soft tissue anchor that includes an elongated shank and an enlarged head, comprising:

a) an outer tube having an elongated bore and proximal and distal end portions;

b) an inner tube that fits the bore of the outer tube, said inner tube having a proximal end, a distal end, a handle and a longitudinal inner tube bore;

c) said inner tube having a plurality of fingers at the distal end portion thereof, said fingers being shaped to grip the soft tissue anchor member at the enlarged head portion thereof;

d) said plurality of fingers being biased to expand radially when moving from a position inside the bore of the larger tube to a position outside the bore of the larger tube;

e) a pushrod slidably disposed within the bore of the inner tube, said pushrod having proximal and distal end portions, said distal end portion having means for engaging said head of said soft tissue anchor;

f) a spring positioned within the inner tube bore, said spring driving the pushrod distally upon retraction of the outer tube relative to the inner tube, so that the pushrod drives the soft tissue anchor free of the fingers when the fingers exit the distal end of the outer tube;

g) wherein the inner tube handle comprises a pair of interlocking members.

16. A soft tissue anchor apparatus comprising:

a) a soft tissue anchor for joining a section of soft tissue to a section of hard tissue, said anchor including an anchor member with a shank, an enlarged head, and a central longitudinal open ended bore;

b) an actuating pin that fits the bore of the anchor member, said pin and the bore of the anchor member being sized and shaped so that the anchor member expands when the actuating pin is driven into the bore;

c) an outer tube having an elongated bore and proximal and distal end portions;

d) an inner tube that fits the bore of the outer tube, said inner tube having a proximal end, a distal end, and a longitudinal inner tube bore;

e) said inner tube having a plurality of fingers at the distal end portion thereof, said fingers being shaped to grip the soft tissue anchor member at the enlarged head portion thereof;

f) said plurality of fingers being expandable after moving from a position inside the bore of the larger tube to a position outside the bore of the larger tube;

g) a pushrod slidably disposed within the bore of the inner tube, said pushrod having proximal and distal end portions, said distal end portion having means for engaging said head of said soft tissue anchor;

h) a spring for driving the pushrod distally upon retraction of the outer tube relative to the inner tube, so that the pushrod drives the soft tissue anchor free of the fingers when the fingers exit the distal end of the outer tube; and i) a spring loading member interlocking with the inner tube to spring load the pushrod by compressing the spring in between the pushrod and the spring loading member.

17. The soft tissue anchor apparatus of claim 16 wherein the outer tube bore is cylindrically shaped with a constant internal diameter.

18. The soft tissue anchor apparatus of claim 16 wherein the fingers are spaced equally about the wall of the inner tube.

19. The soft tissue anchor apparatus of claim 16 wherein there are four of the fingers.

20. The soft tissue anchor apparatus of claim 16 wherein the fingers extend longitudinally from the distal end of the inner tube.

21. The soft tissue anchor apparatus of claim 16 further comprising a pair of handles affixed to the proximal end of the inner tube for manipulating the inner tube relative to the outer tube.

22. The soft tissue anchor apparatus of claim 21 wherein the inner tube handles comprise a pair of interlocking members.

23. The soft tissue anchor apparatus of claim 22 wherein the inner tube handle interlocking members include a first member that is attached to the proximal end of the inner tube and a second member that fits the inner tube bore.

24. The soft tissue anchor apparatus of claim 16 wherein the pushrod comprises an elongated member having a transversely extending flange positioned between the end portions of the elongated member.

25. The soft tissue anchor apparatus of claim 24 wherein the pushrod flange receives one end of the spring during use.

26. The soft tissue anchor delivery apparatus of claim 25 wherein the spring means comprises a coil spring.

27. The soft tissue anchor apparatus of claim 26 wherein the spring is mounted about the elongated member of the pushrod, one end of the spring engaging the flange.

28. The soft tissue anchor delivery apparatus of claim 16 wherein the elongated member has a pair of flanges mounted thereon, one flange positioned between the end portions of the elongated member and a second flange positioned at the distal end of the elongated member, wherein the second flange comprises said means for engaging the head of the soft tissue anchor during use.

29. The soft tissue anchor delivery apparatus of claim 16 further comprising a spring holder that supports the spring during use, said spring and spring holder each fitting the inner tube bore.

* * * * *